United States Patent [19]

Kim et al.

[11] Patent Number: 4,931,281
[45] Date of Patent: Jun. 5, 1990

[54] LAMINAR STRUCTURE FOR ADMINISTERING A CHEMICAL AT A CONTROLLED RELEASE RATE

[75] Inventors: Kwon H. Kim, Bridgewater; Norman L. Henderson, Gladstone; Yie W. Chien, North Brunswick, all of N.J.

[73] Assignee: Hoechst-Roussel Pharmaceuticals Inc., Somerville, N.J.

[21] Appl. No.: 322,605

[22] Filed: Mar. 10, 1989

Related U.S. Application Data

[63] Continuation of Ser. No. 179,184, Apr. 8, 1988, abandoned, which is a continuation of Ser. No. 59,866, Jun. 9, 1987, which is a continuation of Ser. No. 857,000, Apr. 29, 1986, abandoned.

[51] Int. Cl.$^5$ .............................................. A61F 13/02
[52] U.S. Cl. ................................... 424/448; 424/447; 424/449
[58] Field of Search ............... 424/447, 448, 449, 445, 424/409, 414

[56] References Cited

U.S. PATENT DOCUMENTS

4,291,015  9/1981  Keith et al. .......................... 424/486
4,557,934  12/1985  Cooper ................................. 424/449

*Primary Examiner*—Ellis P. Robinson
*Assistant Examiner*—P. L. Prater
*Attorney, Agent, or Firm*—Raymond R. Wittekind

[57] ABSTRACT

A laminar structure for administering a chemical at a controlled release rate is disclosed. The structure comprises a backing member which acts as a boundary through which the chemical does not pass. Contacting at least a portion of the backing member is a chemical containing layer having therein a first chemical portion and a second chemical portion. The first and second chemical portions comprise a mixture of chemical in a first concentration transport mode and a second concentration transport mode. The mixture being in a ratio to give a desired chemical release rate from the chemical containing layer.

11 Claims, 4 Drawing Sheets

LAMINAR STRUCTURE FOR ADMINISTERING A CHEMICAL AT A CONTROLLED RELEASE RATE

This is a continuation of application Ser. No. 179,184 filed Apr. 8, 1988, now abandoned, which is a continuation of application Ser. No. 059,866 filed June 9, 1987, which is a continuation of application Ser. No. 857,000 filed Apr. 29, 1986, now abandoned.

BACKGROUND OF THE INVENTION

1. Field of the Invention

This invention relates to a laminar structure for administering a chemical at a controlled release rate and more particularly, to a structure comprising a layer having therein a first chemical portion and a second chemical portion where the portions comprise a mixture of different transport concentration modes of the chemical.

2. Description of the Prior Art

Controlled drug release devices, in the form of discs, bandages, patches, etc. are presently being employed to treat various diseases. These devices are employed to transdermally administer drugs such as scopolamine, clonidine and nitroglycerin. These devices typically contain a single active drug component dispersed or dissolved in a fluid such as mineral oil, silicone fluid, water, glycerin, etc. and incorporated into a reservoir using a controlled release mechanism, such as for example gel-like matrices fabricated from a combination of polymers and a rate controlling microporous polypropylene membrane, a microporous ethylene-vinyl acetate copolymer membrane, and a micro-sealed silicone matrix. In this regard, the following U.S. Pat. Nos. 3,797,494; 4,294,820; 4,201,211; 3,742,951; 4,336,243; 4,438,139; 4,031,894; 4,436,741; 3,731,683; 3,464,413; 3,426,754; 3,598,123; 3,972,995 describe such time release devices or systems.

Existing time release medicament devices which employ polymeric matrices have as a major drawback the fact that the release rate of active drug or chemical is diminished with time. Accordingly, a constant rate drug delivery system over an extended time period is desired which does not employ (1) a rate-controlling membrane between the drug containing matrix and the skin contact area of the patient, (2) microcapsules for holding and/or releasing the active drug or (3) hydrophilic or hydrophobic solvent systems for dissolving or suspending the drug to be delivered.

SUMMARY OF THE INVENTION

This invention relates to a laminar structure for administering a chemical at a controlled release rate and more particularly, to a structure comprising a chemical containing layer for containing and releasing the chemical, having therein a first chemical portion and a second chemical portion, the first and second chemical portions comprising a mixture of the chemical having different concentration transport modes in a ratio to give a desired chemical release rate from the layer.

The laminar structure has a backing member, which acts as a boundary to the chemical through which the transportation of the chemical does not take place. The chemical containing layer contacts at least a portion of the backing member. To affix the laminar structure to a surface, the structure additionally has an adhesive layer adjacent to the chemical containing layer for fixation contact to the surface.

BRIEF DESCRIPTION OF THE DRAWING

The present invention will be more readily understood by reference to the drawing taken in conjunction with the detailed description wherein.

DETAILED DESCRIPTION

The present invention is described primarily in terms of a medicament comprising the drugs tiamenidine and piretanide. However, it will be understood that such description is exemplary only and is for purposes of exposition and not for purposes of limitation. It will be readily appreciated that the inventive concept described is equally applicable to other drugs, used singly or in combination, as well as other chemicals such as herbicides, pesticides, etc., which are desired to be released at a constant, uniform rate over an extended period of time.

Figure 1:
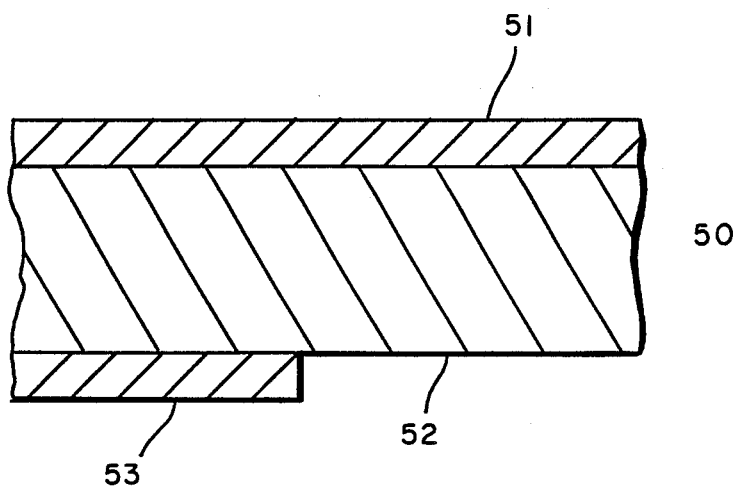
FIG. 1 is a partial cross-sectional view of a laminar structure of the invention for administering a chemical.

Referring to FIG. 1, a laminar structure 50 of the invention is depicted Structure 50 comprises a backing member 51 which is intended to serve as a boundary layer through which the transportation of a selected chemical, e.g. a medicament, herbicide, pesticide, etc. does not take place.

As used herein, the term "chemical" shall mean a medicament or drug used in the treatment of disease, a herbicide, a pesticide or any other chemical entity for which a desired constant and uniform rate of release is desired and includes mixtures of chemicals, including any excipients, carriers, diluents, vehicles, etc. associated therewith for a particular purpose.

Where the chemical intended to be released from structure 50 is non-volatile, member 51 can be fabricated from a porous material, e.g. microporous polyvinyl chloride or polyester film, perforated polyethylene film, perforated polypropylene film, etc. Where the chemical intended to be released from structure 50 is volatile then member 51 must act as a barrier to prevent the selected chemical from being transported therethrough. Accordingly, member 51 is typically fabricated, in this event, of a non-porous material, e.g. aluminum foil, polyethylene film, polypropylene film, and polyester/aluminum foil laminates etc.

Member 51 may be of any thickness depending upon its ultimate use. However, for fabricating a controlled release medicament device, a typical practical thickness has been found to range from 0.01 to 0.1 mm.

Deposited on or in intimate contact with at least a portion of boundary or barrier member 51 is a chemical containing layer 52 for containing and releasing the selected chemical, e.g. tiamenidine, piretanide, intended to be released to a host, e.g. a human or animal patient, a plant, etc., at a controlled and uniform rate over an extended period of time. Layer 52 is fabricated from a selected material which is capable of containing a selected chemical, e.g. a medicament, and which is inert thereto Layer 52 is fabricated from a polymeric material which is inert to the selected chemical, e.g. tiamenidine, piretanide, etc., such as for example polyethylene, polypropylene, ethylene/propylene copolymers and silicone elastomers, such as polydimethylsiloxanes.

In forming layer 52, the selected polymeric material in an uncured or partially cured state is mixed with a suitable chemical mixture whereby a dissolved first chemical mixture portion and a dispersed second chemical mixture portion are present.

By "uncured" or "partially cured" is meant that the polymeric material is in the form of a readily mOldable liquid or semi-solid state, typically paste-like.

The resulting mixture of uncured or partially cured polymeric material and chemical mixture (first and second portions) is then deposited on member 51 and subjected to treatment, e.g. elevated temperature with or without the presence of a catalyst, whereby a fully cured layer 52 is obtained. By "fully cured" is meant that layer 52 forms a uniformly adherent solid layer covering at least a portion of member 51.

In an alternative manner, layer 52 may be formed independently, e.g. by molding, and then laminated to member 51 utilizing procedures and techniques well known in the laminating art.

A suitable chemical mixture comprises a mixture of the chemical active ingredient moiety, in different transportation modes or forms. Thus, the chemical mixture comprises a first form of the chemical active ingredient which is more readily transported, e.g. as by diffusion, through the polymeric layer 52 and a second form of the same chemical active ingredient which is less readily transported than the first form. Typically, for a selected medicament mixture, the active ingredient thereof is in a lipophilic free acid or free base form in combination with the more hydrophilic salt form. By the use of a medicament mixture comprising different transportation modes of active ingredient, it is possible to provide laminar structure 50, having a certain thickness of layer 52, with a medicament release property which is controlled over an extended period of time.

It is to be understood that the concentration of first and second forms of the chemical active ingredient in the first dissolved portion may or may not equal the respective concentrations in the dispersed second portion.

The thickness of layer 52 is a determinative factor for controlling the duration of release of chemical contained therein. The thickness of layer 52 is not critical but depends upon the rate of release desired for a particular chemical contained therein at a particular concentration thereof and a particular ratio of first to second portions of chemical mixture. Typically, layer 52 ranges from 0.01 to 10 mm in thickness. The thickness of layer 52 is selected for a particular chemical, e.g. medicament, at a particular chemical mixture concentration and ratio of first to second portions of chemical mixture whereby the desired release pattern is obtained. In practice such thickness is derived by the use of standard calibration curves using various layer 52 thicknesses with varying chemical mixture concentrations in layer 52 at varying ratios of first portions to second portions It has been discovered that when structure 50 is prepared with a particular dimension of chemical containing layer 52, having first and second portions of chemical mixture dissolved and dispersed therethrough, the chemical, e.g. the active ingredient of the medicament mixture, becomes available at different rates at the site of contact, e.g. with the skin of a patient to be treated.

The amount of the first portion of active ingredient (first transport mode) to the amount of the second portion of active ingredient (second transport mode) ranges in an amount of 0.1 to 99.9% by weight. The ratio of course, will depend upon the particular chemical, e.g., medicament active ingredient, and the rate of release thereof desired or needed In particular, for a particular chemical, e.g. medicament, and polymer system comprising layer 52, a calibration curve is obtained from which the desired delivery of chemical, e.g. active ingredient concentration, with time is ascertained. Typically, various concentrations of chemical mixtures are prepared in layer 52 and the concentration of released chemical, e.g. active ingredient, transported from structure 50 is measured with time using standard methods and techniques known in the art.

It has also been found that the rate of release and duration of release of chemical mixture, e g. medicament, from layer 52 in structure 50 to the receiving body, e.g. patient, is dependent upon the ratio of dissolved chemical mixture to dispersed chemical mixture. Again, using standard methods and techniques, a calibration curve for a particular chemical mixture having varying ratios of first and second dissolved and dispersed portions respectively within layer 52 can be obtained from which a desired release rate for a selected medicament mixture can be ascertained. Typically, for application of a medicament, the ratio of dissolved to dispersed medicament mixture ranges from 999 to 1 to a ratio of 1 to 999 at a thickness of layer 52 of from 0.01 to 10 mm.

Another factor which affects the rate of delivery is the surface area of layer 52 contacting the body to which the chemical is to be delivered. In general, the greater the surface area of layer 52 in contact with the body, e.g. the skin of a patient, the greater is the rate of delivery.

Figure 1A:
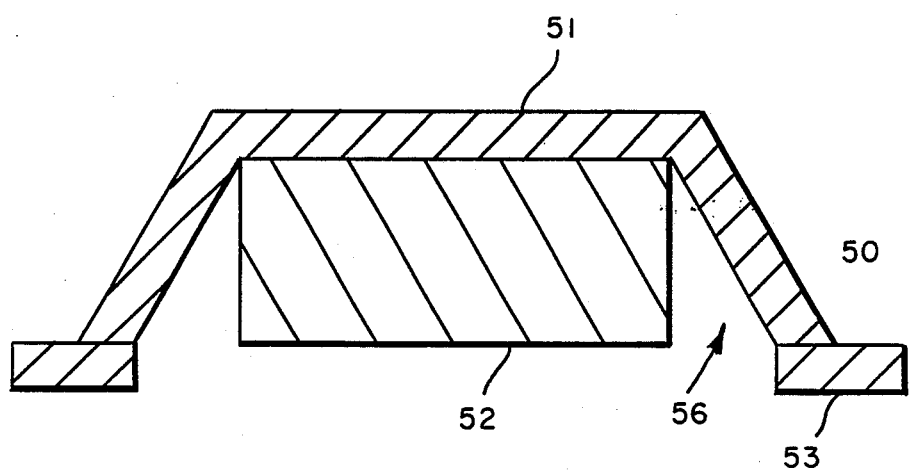
FIG. 1(a) is a partial cross-sectional view of a laminar structure of the invention for administering a chemical.

After forming or depositing layer 52 on member 51. an adhesive layer 53 is applied to the surface of layer 52 as shown in FIG. 1. In an alternative embodiment as shown in FIG. 1(a), adhesive layer 53 is applied directly to layer 51 whereby a space 56 is provided around the periphery of layer 52. Layer 53 is applied to layer 52 or layer 51 to affix structure 50 to a desired surface of a host body, e.g. the skin of a patient. A suitable adhesive is any standard pressure sensitive adhesive employed with, for example, transdermal delivery systems. Some typical suitable adhesives are silicone, polyacrylate, polyisobutylene adhesives, etc.

In operation, structure 50 is applied to a surface of a host body, e.g. the skin of a patient to be treated, by contact with adhesive layer 53. The chemical contained in layer 52 is not transported through barrier member 51 and thus is transported, e.g. by diffusion, through layer 52 and therefrom to the surface of the host body and in the case of animals or humans, when desired, therethrough to the bloodstream. An amount of the first portion of dissolved chemical mixture is released from layer 52 to the host surface whereupon a portion of the second, undissolved and dispersed chemical mixture becomes dissolved in the polymeric material of layer 52. The undissolved and dispersed chemical mixture becomes available for release and serves as a controlled supply.

As indicated, for a given thickness of layer 52, surface area contact of layer 52 and concentration of chemical mixture contained in layer 52, the amount, rate and duration of medicament release is controlled by the ratio of different transportation modes of the chemical mixture in layer 52. Thus the present invention provides a delivery system whose delivery rate can be varied or controlled The present invention thus provides a controlled release of chemical, e.g. medicament active ingredient, over a relatively long period of time.

EXAMPLE 1

A mixture of 2.8 percent by weight of tiamenidine, 0.7 percent by weight of tiamenidine hydrochloride was added to 10 percent by weight of silicone fluid with a viscosity of 100 centistokes. The resultant mixture was stirred at room temperature until a homogeneous slurry was obtained. To the resultant slurry was added 86.0 percent by weight of polydimethyl siloxane elastomer resin and mixing was continued until a homogeneous paste was obtained comprising 10 weight percent of dissolved medicament mixture and 90 weight percent of dispersed, undissolved medicament mixture. A curing agent comprising 0.5 percent by weight of dibutyltindilaurate was added to the paste and mixed at room temperature. The resultant mixture was allowed to cure at room temperature for 24 hours to form a medicament containing polymeric layer destined to be bonded to a selected backing member and destined to have applied to a portion thereof an adhesive layer to form a medicament release device. The dimensions of the polymeric layer in a circular shape were 0.8 mm in thickness and 20 mm in diameter.

EXAMPLES 2-6

The procedure of Example 1 was repeated to obtain polymeric layers having therein medicament mixtures of tiamenidine base to its hydrochloride salt in the following weight percent ratio:
0/100
20/80
50/50
80/20
100/0

Figure 2:
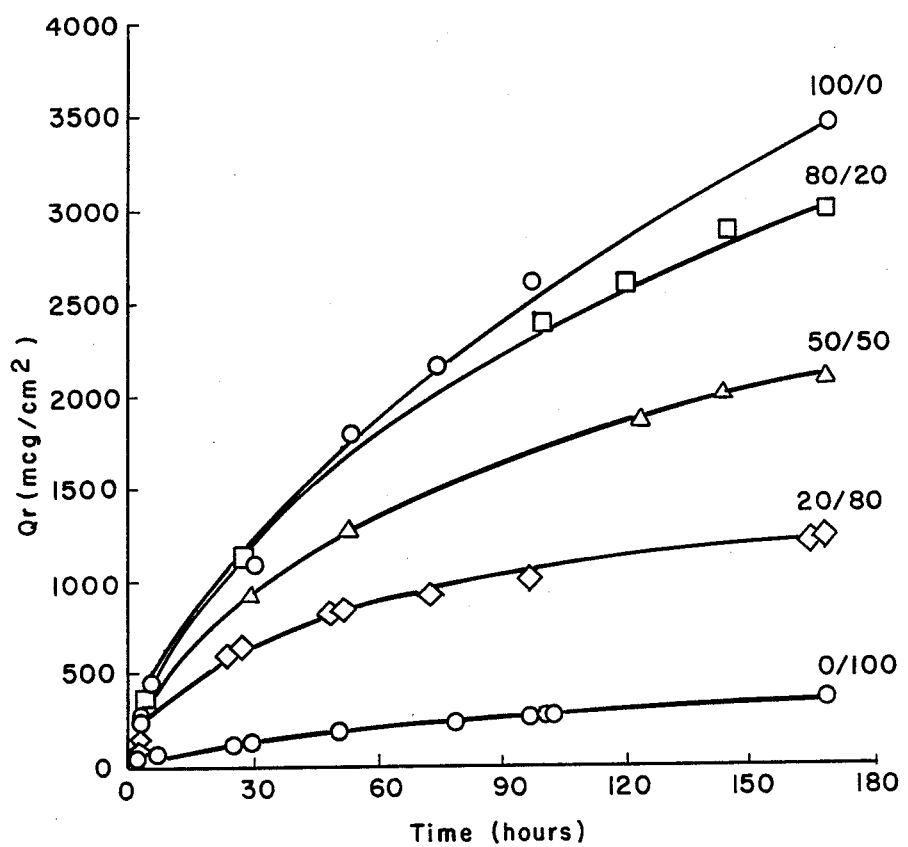
FIG. 2 is a graph depicting the release with time of a first medicament mixture from the laminar structure of FIGS. 1 and 1(a)

Using standard methods in a glass diffusion cell apparatus similar to that described by Franz in the Journal of Investigative Dermatology, Vol. 64, page 190, 1975, the polymeric layers of Examples 1-6 were examined to obtain in-vitro release profiles of the medicament mixture from which a desired release rate could be ascertained. The results of these measurements in terms of amount of medicament released in micrograms per square centimeter with time, in hours, are given in FIG. 2.

EXAMPLES 7-9

The procedure of Examples 1-6 was repeated except that the medicament mixture comprised piretanide and piretanide sodium in the following weight percent concentration ratios:
0/3.5;
3.5/0;
3.5/3.5,
respectively.

Figure 3:
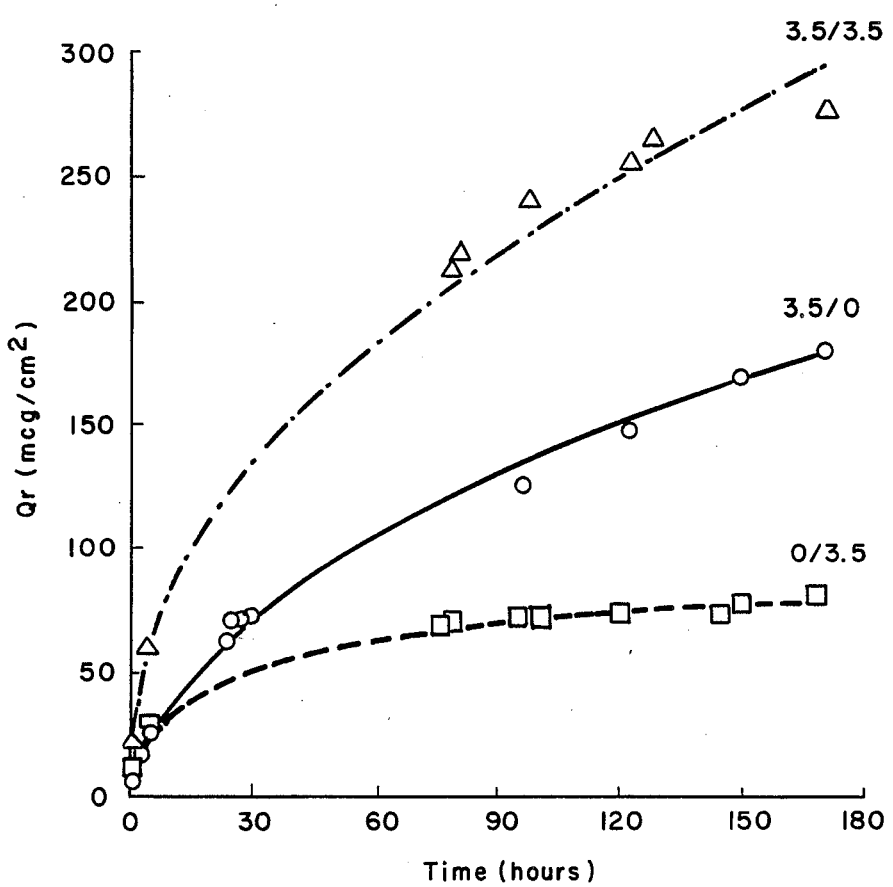
FIG. 3 is a graph depicting the release with time of a second medicament mixture from the laminar structure of FIGS. 1 and 1(a).

The in-vitro release profiles for these medicament mixtures as determined by the method described under Examples 2-6 are given in FIG. 3.

What we claim is:

1. A laminar structure for administering a medicament which comprises:
  a. a boundary layer;
  b. a medicament containing layer contiguous to at least a portion of said boundary layer, for maintaining a supply of the medicament, comprising a polymeric resin matrix having dissolved therein a first portion of a mixture of active ingredients of the medicament dissolved therein and a second portion of said mixture dispersed therethrough, said mixture comprising at least two active ingredients of the medicament having different concentration transport rates through said matrix and present in a ratio to each other to give a controlled release of the medicament selected from the group consisting of tiamenidine and a suitable salt thereof.

2. The structure of claim 1, which additionally comprises an adhesive layer adjacent to said medicament containing layer for affixing the structure to a host body.

3. The structure of claim 1 wherein said mixture contained in said matrix comprises a mixture consisting of tiamenidine and a suitable salt thereof.

4. The structure of claim 1 wherein said matrix comprises a polymeric material selected from the group consisting of polyethylene, polypropylene, ethylene/propylene copolymers, and silicone elastomers.

5. The structure of claim 1 wherein said mixture contained in said matrix comprises a mixture consisting of piretanide and a suitable salt thereof.

6. A method of administering a drug, comprising at least two different forms of active ingredients, to a patient in need thereof which comprises:
  contacting a surface of the body of the patient with a controlled drug release device, said device comprising, a drug containing layer contiguous to said surface for containing and providing a controlled release of the drug, having dissolved and dispersed therethrough a mixture comprising a first form of active ingredient and a second form of active ingredient which differs from said first form in the rate at which it is transported through said layer therefrom to said surface, the ratio of dissolved to dispersed mixture and the ratio of first to second forms being selected to give a desired controlled release rate of the drug from said layer to said surface and whereas the mixture of active ingredients is selected from the groups consisting of tiamenidine and a suitable salt thereof.

7. The method as defined in claim 6 wherein said device further comprises a boundary layer having at least a portion contacting said drug containing layer.

8. The method as defined in claim 7 wherein said device further comprises an adhesive layer adjacent to said drug containing layer to affix said drug containing layer to said surface.

9. The method as defined in claim 7 wherein said device comprises said drug containing layer having a matrix having dissolved therein and dispersed therethrough the drug selected from the group consisting of tiamenidine and a salt thereof.

10. The method as defined in claim 9 wherein said matrix is fabricated from a polymeric resin selected from the group consisting of polyethylene, polypropylene, ethylene/propylene copolymers and silicone elastomers.

11. The method as defined in claim 7 wherein said device comprises said drug containing layer having a matrix having dissolved therein and dispersed therethrough a drug mixture consisting of piretanide and a salt thereof.

* * * * *